(12) United States Patent
Huang

(10) Patent No.: US 7,682,795 B2
(45) Date of Patent: Mar. 23, 2010

(54) METHOD OF DIAGNOSING ALZHEIMER'S DISEASE

(75) Inventor: Yadong Huang, San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 1316 days.

(21) Appl. No.: 10/627,447

(22) Filed: Jul. 24, 2003

(65) Prior Publication Data

US 2004/0157267 A1 Aug. 12, 2004

Related U.S. Application Data

(60) Provisional application No. 60/400,016, filed on Jul. 30, 2002.

(51) Int. Cl.
*G01N 33/53* (2006.01)
(52) U.S. Cl. ..................................... 435/7.1
(58) Field of Classification Search .................. 435/7.1, 435/4, 7.92; 436/517
See application file for complete search history.

(56) References Cited

U.S. PATENT DOCUMENTS

| | | | |
|---|---|---|---|
| 5,492,812 A | 2/1996 | Vooheis | |
| 5,508,167 A * | 4/1996 | Roses et al. | 435/6 |
| 5,545,566 A | 8/1996 | Growden et al. | |
| 5,631,168 A | 5/1997 | Growden et al. | |
| 5,716,828 A | 2/1998 | Roses et al. | |
| 5,811,310 A | 9/1998 | Ghanbari et al. | |
| 5,817,789 A | 10/1998 | Heartlein et al. | |
| 5,849,600 A | 12/1998 | Nixon et al. | |
| 5,942,392 A | 8/1999 | Amouyel et al. | |
| 5,972,634 A | 10/1999 | Tanzi et al. | |
| 5,976,798 A | 11/1999 | Parker et al. | |
| 5,976,817 A | 11/1999 | Davies-Heerema et al. | |
| 5,981,208 A | 11/1999 | Tamburini et al. | |
| 6,027,896 A | 2/2000 | Roses et al. | |
| 6,183,981 B1 | 2/2001 | Gonzalez-Lima | |
| 6,287,793 B1 | 9/2001 | Schenk et al. | |
| 6,300,085 B1 | 10/2001 | Alkon | |
| 6,766,817 B2 | 7/2004 | da Silva | |

FOREIGN PATENT DOCUMENTS

WO WO 02/38108 5/2002

OTHER PUBLICATIONS

Huang et al., "Apolipoprotein E fragments present in Alzheimer's disease brains induce neurofibrillary tangle-like intracellular inclusions in neurons", Proc. Natl. Acad. Sci. USA, 98:8838-8843, (2001).*
Huang et al. (2001) *Proc. Natl. Acad. Sci. USA* 98:8838-8843.
Mahley and Huang (1999) *Curr. Opin. Lipidol*. 10:207-217.
Corder et al. (1993) *Science* 261:921-923.
Slooter et al. (1997) *JAMA* 277 :818-821.
Nicoll et al. (1996) *Neuropathol. Appl. Neurobiol*. 22:515-517.
Huang Y et al. "Bioactive fragments of apolipoprotein E induce neurofibrillary tangles in cultured neurons" Abstracts of the Society for Neuroscience, Society for Neuroscience, Washington, DC, US vol. 26, No. 1-2, 2000, p. 1.
Linton et al. Prevention of atherosclerosis in apolipoprotein e-deficient mice by bone marrow transplantation. Science, 1995, vol. 267, pp. 1034-1037.
Relkin et al. The National institute on aging/alzheimer's association recommendations on the application of apolipoprotein E genotyping to alzheimer's disease. 1996 Ann NY Acad Sci., pp. 149-176.
Brecht, et al. Neuron-Specific Apolipoprotein E4 Proteolysis is Associated with Increased Tau Phosphorylation in Brains of Transgenic Mice. The Journal of Neuroscience, 2004, 24(10):2527-2534.
Linton, et al. Phenotypes of Apolipoprotein B and Apolipoprotein E After Liver Transplantation. J Clin. Invest.1991, vol. 88, pp. 270-281.

* cited by examiner

*Primary Examiner*—Ann Y Lam
(74) *Attorney, Agent, or Firm*—Paul A. Borden; Bozicevic, Field & Francis LLP

(57) ABSTRACT

The present invention provides methods of diagnosing Alzheimer's Disease in a subject. The methods generally involve detecting carboxyl-terminal truncated forms of apoE in a biological sample from the subject. The present invention further provides kits for carrying out the diagnostic methods of the invention.

20 Claims, 1 Drawing Sheet

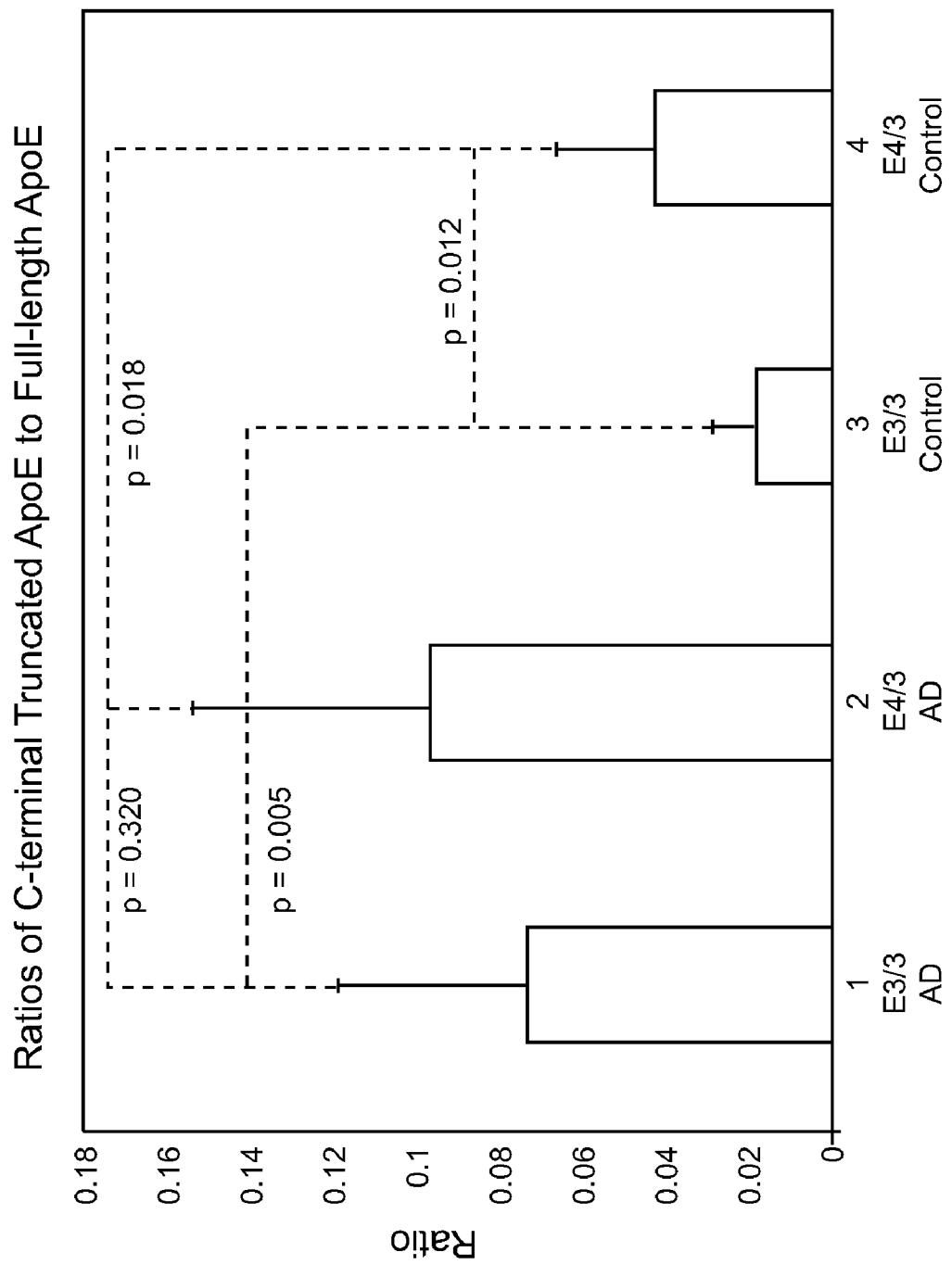

METHOD OF DIAGNOSING ALZHEIMER'S DISEASE

CROSS-REFERENCE

This application claims the benefit of U.S. Provisional Patent Application No. 60/400,016 filed Jul. 30, 2002, which application is incorporated herein by reference in its entirety.

FIELD OF THE INVENTION

The invention relates to apolipoprotein E, and in particular to methods of diagnosing disorders relating to apoE.

BACKGROUND OF THE INVENTION

Human apolipoprotein (apo) E has three major isoforms, apoE2, apoE3, and apoE4. It has been established that apoE4 is associated with increased plasma cholesterol levels and higher risk for the development of coronary heart disease. ApoE4 has also been linked to the pathogenesis of Alzheimer's disease. The apoE4 allele is a major risk factor or susceptibility gene associated with approximately 40-65% of cases of sporadic and familial Alzheimer's disease and it increases the occurrence and lowers the age of onset of the disease. In addition, the apoE4 allele is also associated with poor clinical outcome in patients with acute head trauma and stroke.

Currently, the only means of definitively diagnosing AD is by autopsy. The presence in brain tissue of the plaques and tangles that are the hallmarks of AD can only be seen clearly in post-mortem brain samples. In living subjects, diagnosis of AD is at best a "possible" or "probable" AD. Currently available diagnostic tests for AD include neuropsychological tests, which measure memory, problem solving, attention, counting, and language; and brain scans. Complicating the diagnosis of AD is the fact that some of the symptoms, such as memory loss, are also associated with other, unrelated disorders.

There is a need in the art for a diagnostic assay for AD that is more accurate and reliable than current diagnostic methods, and which can be performed on living subjects. The present invention addresses this need.

Literature

Huang et al. (2001) *Proc. Natl. Acad. Sci. USA* 98:8838-8843; Mahley and Huang (1999) *Curr. Opin. Lipidol.* 10:207-217; Corder et al. (1993) *Science* 261:921-923; Slooter et al. (1997) *JAMA* 277:818-821; and Nicoll et al. (1996) *Neuropathol. Appl. Neurobiol.* 22:515-517; U.S. Pat. Nos. 6,358,681, 6,300,085, 6,287,793, 6,183,981, 5,981,208, 5,976,817, 5,976,798, 5,972,634, 5,942,392, 5,849,600, 5,811,310, 5,631,168, 5,545,566 and 5,492,812.

SUMMARY OF THE INVENTION

The present invention provides methods of diagnosing Alzheimer's Disease in a subject. The methods generally involve detecting carboxyl-terminal truncated forms of apoE in a biological sample from the subject. The present invention further provides kits for carrying out the diagnostic methods of the invention.

FEATURES OF THE INVENTION

The present invention features methods for diagnosing Alzheimer's Disease in an individual. The methods generally involve detecting carboxyl-terminal truncated apoE in a biological sample from the individual. In some embodiments, the biological sample is blood, or serum. In some embodiments, the carboxyl-terminal truncated apoE has a molecular weight of about 14-20 kDa. In some embodiments, the apoE is apoE4. In other embodiments, the apoE is apoE3. In other embodiments, the apoE is a mixture of apoE3 and apoE4.

The detection step in some embodiments involves detecting a level of carboxyl-terminal truncated apoE in the bodily fluid. In some of these embodiments, the method further involves detecting a level of full length apoE in the biological sample from the individual. A ratio of the level of carboxyl-terminal truncated apoE compared to the level of full length apoE in the biological sample that is greater than a ratio associated with a control biological sample from an individual not having Alzheimer's Disease is indicative of a diagnosis of Alzheimer's Disease. For example, in some embodiments, the ratio is greater than about 1.5, greater than about 2, or greater than about 3.

The present invention further provides a kit for diagnosing Alzheimer's Disease, the kit comprising an antibody that binds to carboxyl-truncated apoE and instructions for using the antibody for diagnosing Alzheimer's Disease. In some embodiments, the antibody is attached to a solid support. In some embodiments, the kit further includes an antibody that specifically binds to a carboxyl-terminal portion of apoE.

BRIEF DESCRIPTION OF THE DRAWING

The figure is a bar graph depicting ratios of C-terminal truncated apoE to full length apoE in experimental and control samples.

DEFINITIONS

The term "Alzheimer's disease" (abbreviated herein as "AD") as used herein refers to a condition associated with formation of neuritic plaques comprising amyloid β protein primarily in the hippocampus and cerebral cortex, as well as impairment in both learning and memory. "AD" as used herein is meant to encompass both AD as well as AD-type pathologies.

As used herein, the terms "determining," "measuring," and "assessing," and "assaying" are used interchangeably and include both quantitative and qualitative determinations.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

The terms "subject," "host," "patient," and "individual" are used interchangeably herein to refer to any mammalian subject for whom diagnosis or therapy is desired, particularly humans. Other subjects may include cattle, non-human primates, dogs, cats, guinea pigs, rabbits, rats, mice, horses, and so on.

As used herein, the term "purified" refers to a compound (e.g., either a polynucleotide or a polypeptide) that is removed from its natural environment and is at greater concentration than it is in its natural environment. A composition comprising purified apoE typically is a composition comprising less than about 20%, less than about 15%, less than about 10%, less than about 5%, less than about 2%, less than about 1%, less than about 0.5%, or less than about 0.1% other components (e.g., macromolecules other than apoE) with which apoE is naturally associated. Thus, purified apoE is at least about 80%, at least about 90%, at least about 95%, at least about 98%, or at least about 99%, or greater, pure.

The term "binds specifically," in the context of antibody binding, refers to high avidity and/or high affinity binding of an antibody to a specific polypeptide i.e., epitope of an apoE polypeptide. Antibody binding to an epitope on a specific apoE polypeptide or fragment thereof is stronger than binding of the same antibody to any other epitope, particularly those which may be present in molecules in association with, or in the same sample, as the specific polypeptide of interest, e.g., binds more strongly to a specific apoE epitope than to a different apoE epitope so that by adjusting binding conditions the antibody binds almost exclusively to the specific apoE epitope and not to any other apoE epitope, and not to any other apoE polypeptide (or fragment) which does not comprise the epitope. Antibodies which bind specifically to a polypeptide may be capable of binding other polypeptides at a weak, yet detectable, level (e.g., 10% or less of the binding shown to the polypeptide of interest). Such weak binding, or background binding, is readily discernible from the specific antibody binding to a subject polypeptide, e.g. by use of appropriate controls. In general, specific antibodies bind to a apoE polypeptide with a binding affinity of $10^{-7}$ M or more, e.g., $10^{-8}$ M or more (e.g., $10^{-9}$ M, $10^{-10}$, $10^{-11}$, etc.). In general, an antibody with a binding affinity of $10^{-6}$ M or less is not useful in that it will not bind an antigen at a detectable level using conventional methodology currently used.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "antibody" includes a plurality of such antibodies and reference to "the carboxyl-truncated apoE" includes reference to one or more the carboxyl-truncated apoEs and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of diagnosing Alzheimer's Disease (AD) in a subject. The methods generally involve detecting a carboxyl-terminal truncated form of apoE in a biological sample from the subject. The present invention further provides kits for carrying out the diagnostic methods of the invention.

The methods of the invention may be performed on biological samples from living subjects, or may be carried out post mortem on tissues or fluids from deceased subjects. A particularly advantageous feature of the invention is that diagnosis can be made using aqueous biological tissues, such as blood and serum, which are readily available for sampling from a living subject. Thus, a diagnosis for AD can be made on a living subject, using readily available biological samples.

The methods of the invention are also useful for determining a patient's response to a treatment for AD; for determining the severity of the disease; and for monitoring the progression of the disease.

Methods of Detecting Carboxyl-Truncated apoE in a Biological Sample

The present invention provides methods of diagnosing AD in a subject; methods of determining a patient's response to a treatment for AD; methods for determining the severity of AD; and methods for monitoring the progression of AD. The methods generally involve detecting a carboxyl-terminal truncated form of apoE ("carboxyl-truncated apoE") in a biological sample from the subject. In some embodiments, the amount of carboxyl-truncated apoE in the sample is determined. In other embodiments, the level of carboxyl-truncated apoE in a biological sample is determined and compared to the level of full-length apoE in the sample; and the ratio of carboxyl-truncated apoE to full-length apoE is calculated. A ratio of carboxyl-truncated apoE:full-length apoE that is above a control ratio indicates that the individual has AD. In other embodiments, the level of carboxyl-truncated apoE in a biological sample is determined, and compared to the total amount of apoE in the sample; and the ratio of carboxyl-truncated apoE to the total amount of apoE is calculated. A ratio of carboxyl-truncated apoE to total apoE that is above a control ratio indicates that the individual has AD. A control ratio is a ratio associated with a biological sample from an individual who does not have AD.

Carboxyl-truncated apoE

Carboxyl-truncated apoE is detected in a biological sample from an individual. In general, carboxyl-truncated apoE is detected using an antibody that binds to a carboxyl-truncated form of apoE.

ApoE is synthesized as a pre-polypeptide that is processed into a mature apoE polypeptide that is approximately 34 kDa protein of about 299 amino acids in length. "Full-length" apoE, as used herein, refers to a mature, 34 kDa protein of about 299 amino acids. The term "carboxyl-truncated form of apoE" refers to truncated forms of the 34 kDa full-length apoE protein that comprise carboxyl-terminal truncations of the full-length mature apoE. The amino acid sequences of ApoE pre-polypeptide and mature polypeptides are provided in GenBank accession number AAB59518.

Human apoE occurs as three major isoforms: apoE2, apoE3, and apoE4. The methods of the invention provide for detection of carboxyl-truncated forms of apoE, regardless of the isoform, e.g., the methods of the invention provide for detection of carboxyl-truncated forms of apoE2, apoE3, and apoE4. Thus, depending on the genotype of the individual being tested, carboxyl-truncated forms of one or more isoforms of apoE are detected.

Carboxyl-truncated forms of apoE that are detected using the methods of the invention include, but are not limited to, apoE that has a deletion of from about 10 to about 15, from about 15 to about 20, from about 20 to about 25, from about from about 25 to about 28, from about 28 to about 30, from about 30 to about 35, from about 35 to about 40, from about 40 to about 45, or from about 45 to about 48 amino acids from the carboxyl terminus of apoE. In many embodiments, carboxyl-terminal truncated apoE polypeptides include at least amino acids 244-260 of apoE.

In some embodiments, carboxyl-truncated forms of apoE that are detected using the methods of the invention have, in addition to the above-mentioned deletion of carboxyl-terminus amino acids, truncations at the amino terminus of from about to 10 to about 100 amino acids, e.g., from about 10 to about 15, from about 15 to about 20, from about 20 to about 25, from about from about 25 to about 28, from about 28 to about 30, from about 30 to about 35, from about 35 to about 40, or from about 40 to about 50, from about 50 to about 60, from about 60 to about 70, from about 70 to about 80, from about 80 to about 90, or from about 90 to about 100 amino acids.

Carboxyl-truncated forms of apoE that are detected using the methods of the invention have molecular weights of from about 13 kD to about 31 kD, e.g., from about 13 kD to about 15 kD, from about 15 kD to about 17 kD, from about 17 kD to about 20 kD, from about 28 kD to about 31 kD, or from about 29 kD to about 30 kD. In some embodiments, carboxyl-truncated forms of apoE that are detected using the methods of the invention have a molecular weight in the range of from about 14 kD to about 20 kD.

A 29-30 kD carboxyl-truncated form of apoE has a C-terminal truncation of from about 25 to about 35, from about 27 to about 33, or from about 29 to about 31 amino acids, when compared to full-length apoE.

A 14-20 kD carboxyl-truncated form of apoE has a C-terminal truncation of from about 25 to about 35, from about 27 to about 33, from about 29 to about 31, from about 31 to about 35, from about 35 to about 40, or more, amino acids when compared to full-length apoE; and may in addition have an N-terminal truncation of from about 10 to about 45 or more amino acids, e.g., from about 10 to about 15, from about 15 to about 20, from about 20 to about 25, from about from about 25 to about 28, from about 28 to about 30, from about 30 to about 35, from about 35 to about 40, or from about 40 to about 45, or more, amino acids, when compared to full-length apoE.

Detection of carboxyl-truncated apoE is generally carried out using an antibody that binds to carboxyl-truncated apoE. Antibodies to carboxyl-truncated apoE are generated as described below.

Separating carboxyl-truncated apoE

In general, methods of the invention involve separating carboxyl-truncated apoE from full-length apoE. Carboxyl-truncated apoE can be separated from full-length apoE on the basis of size (e.g., molecular weight); charge properties (e.g., isoelectric point); or immunological properties (e.g., the presence of an epitope(s) recognized by an antibody specific for the epitope(s)).

In some embodiments, carboxyl-truncated apoE is separated from full-length apoE on the basis of immunological properties. In some of these embodiments, a biological sample comprising apoE is contacted with an antibody specific for the carboxyl-terminal portion of apoE. Antibody specific for the C-terminal portion of apoE binds full-length apoE, as well as any C-terminal fragments that might be present, forming a complex. Once the anti-C-terminal apoE antibody/full-length apoE complex is formed, the complex is removed or separated from the remainder of the sample.

In some embodiments, the complex forms a precipitate, and the precipitate is separated from the remainder of the sample by centrifugation or filtration. In some of these embodiments, a second antibody, e.g., an anti-isotype antibody that binds the anti-C-terminal apoE antibody, is contacted with the sample.

In other embodiments, the anti-C-terminal apoE antibody is bound, directly or via a linker, to an insoluble support. Insoluble supports are known in the art and include, but are not limited to, a bead (e.g, magnetic beads, polystyrene beads, and the like); a membrane; and the like. In one non-limiting example, the anti-C-terminal apoE antibody is bound to a magnetic bead. The anti-C-terminal apoE antibody bound to the magnetic bead is contacted with the sample, and, after a complex is formed between the antibody and any apoE in the sample, a magnetic field is applied, such that the complex is removed from the sample. Where the antibody is bound to an insoluble support, such as a membrane, anti-C-terminal apoE antibody/apoE complex bound to the membrane-bound antibody is removed from the sample by removing the membrane, or by transferring the sample to a separate container. Where the antibody is bound to a bead, anti-C-terminal apoE antibody/apoE complex bound to the bead is removed from the sample by centrifugation or filtration.

In other embodiments, a member of a specific binding pair is bound to an insoluble support, and the anti-C-terminal apoE antibody is linked to a second member of the specific binding pair. Specific binding molecules include pairs, such as biotin and streptavidin, digoxin and antidigoxin, etc. In other embodiments, protein A is bound to the insoluble support, and the anti-C-terminal apoE is of an isotype that binds protein A.

In other embodiments, carboxyl-truncated apoE is separated from full-length apoE on the basis of size (e.g., molecular weight). In some of these embodiments, carboxyl-truncated apoE is separated from full-length apoE by electrophoresis. In some embodiments, a sample is loaded onto a sodium dodecyl sulfate-polyacrylamide gel electrophoresis (SDS-PAGE) gel. The sample is subjected to electrophoresis, after which the separated proteins are transferred to a membrane (e.g., nylon, nitrocellulose, polyvinylpyrrolidone, and the like), and the membrane is probed with an antibody, using standard methods, as described below.

Other methods for separating carboxyl-truncated apoE from full-length apoE on the basis of size include, but are not limited to, size exclusion chromatography; gel filtration, and size cutoff membrane filtration.

In other embodiments, carboxyl-truncated apoE is separated from full-length apoE on the basis of charge (e.g., isoelectric point), or by the performance of the polypeptides in during other chromatographic systems e.g. ion exchange chromatography, high performance liquid chromatography, heparin-based columns, etc.

In general, a suitable separation means is used with a suitable platform for performing the separation. For example, where carboxyl-truncated apoE is separated by binding to antibodies that bind to the carboxy terminal portion of apoE, the separation is performed using any of a variety of methods, including, but not limited to, affinity column chromatography, capillary action or lateral flow test strips, immunoprecipitation, etc. Where carboxyl-truncated apoE is separated from full length apoE by size, the separation is performed using any of a variety of methods, including, but not limited to, size exclusion chromatography, gel filtration, size-cutoff membrane filtration, and electrophoresis. Separation means may also be combined in a single platform, for example size separation may be combined with separation based on charge in two-dimensional PAGE.

In many embodiments, carboxyl-truncated apoE is separated from full-length apoE by applying the sample to one end of a test strip, and allowing the proteins to migrate by capillary action or lateral flow. Methods and devices for lateral flow separation, detection, and quantitation are known in the art. See, e.g., U.S. Pat. Nos. 5,569,608; 6,297,020; and 6,403,383. In these embodiments, a test strip comprises, in order from proximal end to distal end, a region for loading the sample (the sample-loading region); a first test region comprising a bound antibody specific for the C-terminal portion of apoE; and a second test region comprising a bound antibody specific for carboxyl-truncated apoE. The sample is loaded on to the sample-loading region, and the proximal end of the test strip is placed in a buffer. Full-length apoE is captured by the bound antibody in the first test region, and carboxyl-truncated apoE is captured by the bound antibody in the second test region. Detection of the captured apoE is carried out as described below. For example, detection of captured apoE is carried out using detectably labeled antibody specific for an epitope of apoE that is common to both carboxyl-truncated apoE and full-length apoE.

In other embodiments, carboxyl-truncated apoE is separated from full-length apoE by applying the sample to an affinity chromatography column, and allowing the proteins to migrate through the column through gravity or centrifugal force. In these embodiments, the column comprises, in order from proximal to distal, a region for loading the sample, and a first region comprising a bound antibody that binds to carboxyl-truncated apoE. The test sample is loaded onto the sample loading region and the sample is allowed to travel through the column by gravity or with centrifugal or vacuum assistance. Full-length apoE is captured by the bound antibody in the first region and carboxyl-truncated apoE passes through the column and is found in the eluate. Suitable washes may also be performed, and captured apoE may be eluted using suitable elution buffers.

In other embodiments, carboxyl-truncated apoE is separated from full-length apoE by applying a sample to an aqueous solution comprising an antibody specific for the C-terminus of apoE bound to an insoluble support such as a bead; mixing and incubating the beads and sample to allow binding and capture of the full length apoE to the beads; and separating the beads from solution by centrifugation, gravity, or, if the beads are magnetic, by applying a magnetic field. Suitable washes may also be performed, and captured apoE may be eluted using suitable elution buffers.

In embodiments that involve immunoprecipitation, aqueous test samples are contacted with antibody that specifically bind a C-terminal region of apoE and incubated to allow binding of the full length apoE to the antibody. Protein A, which binds to the constant region of an antibody to form a complex that can be precipitated, is then added, forming an antibody/full-length apoE/Protein A complex; and the antibody/full-length apoE complex is precipitated. Complexed antibody/full-length apoE/Protein A is then removed by the solution by centrifugation, leaving the truncated apoE in solution.

In some embodiments, the means for separating carboxyl-truncated apoE from full length apoE is combined with suitable means for detecting and quantitating carboxyl-truncated apoE.

Detecting and Quantitating carboxyl-truncated apoE

Once carboxyl-truncated apoE is separated from full-length apoE, carboxyl-truncated apoE is detected and/or the level or amount of carboxyl-truncated apoE is determined (e.g., measured). Carboxyl-truncated apoE is generally detected using an antibody specific for carboxyl-truncated apoE.

Detection with a specific antibody is carried out using well-known methods. In general, the antibody is detectably labeled, either directly or indirectly. Direct labels include radioisotopes (e.g., $^{125}$I; $^{35}$S, and the like); enzymes whose products are detectable (e.g., luciferase, β-galactosidase, horse radish peroxidase, alkaline phosphatase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin; fluorescent proteins; and the like. Fluorescent proteins include, but are not limited to, a green fluorescent protein (GFP), including, but not limited to, a "humanized" version of a GFP, e.g., wherein codons of the naturally-occurring nucleotide sequence are changed to more closely match human codon bias; a GFP derived from *Aequoria victoria* or a derivative thereof, e.g., a "humanized" derivative such as Enhanced GFP, which are available commercially, e.g., from Clontech, Inc.; a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973; and the like.

Indirect labels include second antibodies specific for apoE-specific antibodies, wherein the second antibody is labeled as described above; and members of specific binding pairs, e.g., biotin-avidin, and the like.

In some embodiments, carboxyl-truncated apoE is quantitated. Quantitation can be carried out using any known method, including, but not limited to, enzyme-linked immunosorbent assay (ELISA); radioimmunoassay (RIA); and the like. In general, quantitation is accomplished by comparing the level of expression product detected in the sample with the amount of carboxyl-truncated apoE present in a standard curve.

In some embodiments, total apoE (e.g., including full-length apoE and any apoE fragments present) is separated (e.g., isolated) from other components (e.g., proteins and other macromolecules) of the sample before analysis. The isolated total apoE can then be subjected to any of the separation methods described above. In some embodiments, the isolated total apoE is applied to a gel and the carboxyl-truncated apoE is separated from full-length apoE. After separation, the gel is stained, and densitometric analysis applied to quantitate the carboxyl-truncated apoE.

In some embodiments, carboxyl-truncated apoE is separated on a test strip, as described above. In these embodiments, carboxyl-truncated apoE is detected using a detectably labeled antibody that binds carboxyl-truncated apoE. The test strip can also be developed using an antibody that detects both carboxyl-truncated apoE and full-length apoE. Carboxyl-truncated apoE can be quantitated using a reflectance spectrophotometer.

In some embodiments, carboxyl-truncated apoE is directly detected, using a detectably labeled antibody that binds carboxyl-truncated apoE with a higher affinity than full-length apoE. For example, an antibody is used that binds carboxyl-truncated apoE with an affinity that is at least about 5-fold, at least about 10-fold, at least about 25-fold, at least about 50-fold, or at least about 100-fold, or higher, than the affinity for full-length apoE. Detection methods include ELISA, RIA, and other assays as described above.

Determining the Proportion of carboxyl-truncated apoE in a Sample

In some embodiments, the proportion of carboxyl-truncated apoE in a sample is determined. In some embodiments, the ratio of carboxyl-truncated apoE to full-length apoE is determined. In other embodiments, the ratio of carboxyl-truncated apoE to total apoE present in the sample is determined.

In some embodiments, the ratio of carboxyl-truncated apoE to full-length apoE is determined. In some of these embodiments, the level of full-length apoE is determined using an antibody specific for the carboxyl-terminal portion of apoE that is absent from the carboxyl-truncated apoE, e.g., an antibody specific for a C-terminal fragment of full-length apoE, including, but not limited to, a fragment consisting of amino acids 277-299, or variants of the 272-299 fragment having N-terminal and/or C-terminal truncations of from about 1 to about 15 amino acids, e.g., amino acids 275-299, amino acids 280-299, amino acids 272-295, amino acids 272-290, and the like.

Once the amount of full-length apoE in the sample is determined, carboxyl-truncated apoE is separated from the sample, and the level of carboxyl-truncated apoE is quantitated. The ratio of carboxyl-truncated apoE to full-length apoE is then calculated.

In some embodiments, a sample is applied to a gel and the proteins are separated electrophoretically, then transferred to a membrane, using methods standard in the art. Full-length apoE and carboxyl-truncated apoE on the membrane are visualized using antibodies specific for full-length apoE and for carboxyl-truncated apoE. Alternatively, full-length apoE and carboxyl-truncated apoE are visualized on the membrane using an antibody that binds both full-length apoE and carboxyl-truncated apoE. The ratio of carboxyl-truncated apoE to full-length apoE is then determined by scanning the gel with a densitometer and determining the relative amounts of full-length apoE and carboxyl-truncated apoE on the membrane.

In some embodiments, the ratio of carboxyl-truncated apoE to total apoE is determined. In these embodiments, total apoE is determined using any known method. For example, total apoE can quantitated, using an antibody that binds to full-length apoE, as well as fragments of apoE such as 29-30 kD apoE, 14-20 kD apoE, and N-terminal and C-terminal cleavage fragments resulting from production of 29-30 kD apoE and 14-20 kD apoE. A suitable antibody is a polyclonal antibody that binds multiple epitopes on apoE. Polyclonal anti-apoE antibodies are available commercially; and can be readily generated using standard methods that are well known in the art. Total apoE can be quantitated either with or without prior isolation of total apoE from the sample.

After the total apoE is quantitated, carboxyl-truncated apoE is separated from the sample, as described above, and the level of carboxyl-truncated apoE is determined, as described above. The ratio of carboxyl-truncated apoE to total apoE is then calculated.

Antibodies

In many embodiments of the invention, full-length apoE is separated from carboxyl-truncated apoE using antibodies that specifically bind to a C-terminal region of apoE that is present in the full-length apoE but not in the carboxyl-truncated apoE. In some embodiments, full-length apoE is specifically detected using antibody that binds specifically to a C-terminal region of apoE that is present in full-length apoE but not in carboxyl-truncated apoE. In other embodiments, antibodies that bind carboxyl-truncated apoE are used to detect carboxyl-truncated apoE. Antibodies that bind carboxyl-truncated apoE also bind full-length apoE; thus, such antibodies detect both full-length and carboxyl-truncated apoE. Antibodies that bind carboxyl-truncated apoE are generally used to detect full-length apoE and/or carboxyl-truncated apoE after carboxyl-truncated apoE is separated from full-length apoE.

Antibodies Specific for C-terminal Region of apoE

In many embodiments, an antibody specific for the C-terminal region of apoE is used. By "specific for the C-terminal region of apoE" is meant that the antibody does not detectably bind the 29-30 kD or the 14-20 kD carboxyl-truncated fragments of apoE.

Antibody specific for the C-terminal portion of apoE specifically binds an epitope(s) within a C-terminal region of from about amino acid 270 to about amino acid 299 of mature, full-length apoE, e.g., the antibody binds an epitope within a C-terminal region of from about amino acid 270 to about amino acid 280, from about amino acid 272 to about amino acid 299, from about amino acid 280 to about amino acid 299, or from about amino acid 290 to about amino acid 299.

In some embodiments, antibodies specific for the C-terminal region of apoE are raised against a C-terminal immunogenic fragment of apoE, where the fragment is of up to about 10 amino acids in length, up to about 15 amino acids in length, up to about 20 amino acids in length, up to about 30 amino acids in length, up to about 50 amino acids in length, or up to about 100 amino acids in length. In many embodiments, antibodies are raised against the C-terminal 28 amino acid residues of apoE, as described by GenBank accession number AAB59518.

An antibody specific for the C-terminal region of apoE may also be made by purifying the antibody from a population of antibodies raised against full-length apoE using its binding affinity for the C-terminal region of apoE. In this embodiment, the antibody population is passed through a column containing a C-terminal fragment of apoE bound to the column and the antibodies specific for the C-terminal region are specifically bound and retained by the column whereas other antibodies are not bound and retained by the column. Antibodies that are specific for the C-terminal region of apoE that are bound to the column may be released using any suitable change in the column chemical environment e.g. salt conditions.

In a further embodiment, an antibody specific for the C-terminal region of apoE is purified from a population of antibodies raised against full-length apoE using its binding affinity for the C-terminal region of apoE. In this embodiment, the antibody population is passed through a column containing an N-terminal fragment of apoE bound to the column, the antibodies specific for the C-terminal region do not bind and are not retained by the column whereas other antibodies specific for apoE are bound and retained by the column. In this embodiment, antibodies specific for the C-terminal region are found in the column flow-through. In an exemplary embodiment, antibodies raised against full-length apoE are bound to apoEΔ 277-299, e.g., a polypeptide containing amino acids 1-271 of mature, full-length apoE. Antibodies that do not bind to apoEΔ 272-299 are specific for a C-terminal portion of apoE.

Antibodies that Bind to carboxyl-truncated apoE

In other embodiments, an antibody that binds to carboxyl-truncated apoE_is used. By "binds to carboxyl-truncated apoE" is meant that the antibody detectably binds both full length and carboxyl-truncated fragments of apoE (including 14-20 kD and 29-30 fragments of apoE).

In one embodiment, an antibody that binds to carboxyl-truncated apoE is an antibody raised against a fragment of carboxyl-truncated apoE, where the fragment is from about 10 amino acids to about 200 amino acids in length, e.g., a fragment of up to about 10 amino acids in length, up to about 15 amino acids in length, up to about 20 amino acids in length, up to about 30 amino acids in length, up to about 50 amino acids in length, up to about 100 amino acids in length, or up to about 200 amino acids in length, where the fragment is derived from a region of from about amino acid 50 to about amino acid 270, from about amino 50 to about amino acid 200, from about amino acid 75 to about amino acid 270, from about amino acid 75 to about amino acid 250, or from about amino acid 100 to about amino acid 270 of mature full-length apoE. In many embodiments, antibodies are raised against the N-terminal 271 amino acid residues of mature apoE, as described by GenBank accession number AAB59518. In some embodiments, an antibody that binds carboxyl-truncated apoE binds to an epitope within amino acids 244-260 of apoE.

An antibody that binds to carboxyl-truncated apoE may also be made by purifying the antibody from a population of antibodies raised against full-length apoE using its binding affinity for carboxyl-truncated apoE. In this embodiment, the antibody population is passed through a column containing a carboxyl-truncated apoE polypeptide bound to the column and the antibodies that bind carboxyl-truncated apoE are specifically bound and retained by the column whereas other antibodies are not bound and retained by the column. Antibodies that bind carboxyl-truncated apoE that are bound to the column may be released using any suitable change in the column chemical environment e.g. salt conditions.

In a further embodiment, an antibody that binds carboxyl-truncated apoE is purified from a population of antibodies raised against full-length apoE using its binding affinity for carboxyl-truncated apoE. In this embodiment, the antibody population is passed through a column containing N-terminally-truncated apoE bound to the column and the antibodies that bind the carboxyl-truncated apoE do not bind and are not retained by the column whereas other antibodies specific for apoE are bound and retained by the column. In this embodiment, antibodies that bind the carboxyl-truncated apoE are found in the column flow-through.

In many embodiments, antibodies that bind the carboxyl-truncated apoE are antibodies raised against the full-length apoE polypeptide, as described by GenBank accession number AAB59518.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate.

For monoclonal antibodies (MAbs), after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, New York, 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage display libraries, usually in conjunction with in vitro affinity maturation.

Antibodies that bind to apoE polypeptides are usually produced by immunization of non-human animals with the isolated polypeptides and, if monoclonal antibodies are desired, production of hybridomas. Each of these steps is described below.

Antibodies specific to full length or carboxyl-truncated apoE are produced by immunizing an immunocompetent non-human mammal (e.g., murine, rodentia, lagomorpha, ovine, porcine, bovine, etc.) with apoE polypeptide that has been made using recombinant or non-recombinant means. Immunization and hybridoma production with the apoE can be accomplished according to conventional methods well known in the art. Immunizations are generally performed in accordance with conventional techniques, where the animals may be injected subcutaneously, intramuscularly, intraperitoneally, intravascularly, etc.

Immunizations may be divided up into 1 or more injections, usually not more than about 8 injections, over a period of from about one to three weeks. The injections may be with or without adjuvant, e.g. complete or incomplete Freund's adjuvant, specol, alum, etc.

Either monoclonal or polyclonal antibodies, preferably monoclonal antibodies (MAbs), are produced from the immunized animal. Polyclonal antisera may be harvested from serum in accordance with conventional methods after completion of the immunization schedule. For production of MAbs, lymphocytes are harvested from the appropriate lymphoid tissue, e.g. spleen, draining lymph node, etc., and fused with an appropriate fusion partner, usually a myeloma line, producing a hybridoma secreting a specific monoclonal antibody. Methods for hybridoma production are well known in the art (see, e.g., *Antibodies, A Laboratory Manual*, Harlow & Lane eds., (1988) Cold Spring Harbor Press).

The antibodies and MAbs utilized in the present invention can be modified in any of a variety of ways, with the proviso that the modified MAbs retain substantially specific binding to the original antigen (e.g., to apoE). The ability of such modified antibodies to specifically and sensitively bind their original antigen can be assessed in in vitro assays as described herein e.g. western blotting, ELISA, etc. Such screening is routine and, with the guidance provided herein, within the skill of the ordinarily skilled artisan.

Modified antibodies used by the present invention include those produced using biochemical, chemical, or recombinant DNA techniques. For example, antibody fragments, such as Fv, F(ab')$_2$ and Fab may be prepared from the antibodies of the invention by cleavage of the intact protein, e.g., by protease or chemical cleavage.

Alternatively, a truncated gene is designed. For example, a chimeric gene encoding a portion of the F(ab')$_2$ fragment would include DNA sequences encoding the $C_{H1}$ domain and hinge region of the H chain, followed by a translational stop codon to yield the truncated molecule. Generally, such antibody fragments retain antigen avidity and/or affinity that is substantially the same as the original antibody from which they are derived.

The antibodies may also be produced as a single chain, instead of the normal multimeric structure. Single chain antibodies are described in Jost et al. (1994) *J. Biol. Chem.* 269:26267-73, and others. DNA sequences encoding the variable region of the heavy chain and the variable region of the light chain are ligated to a spacer encoding at least about four amino acids of small neutral amino acids, including glycine and/or serine. The protein encoded by this fusion allows assembly of a functional variable region that retains the specificity and affinity of the original antibody.

The antibodies utilized in the present invention may also be humanized. Methods of humanizing antibodies are well known in the art. The humanized antibody may be the product of an animal having transgenic human immunoglobulin (Ig) constant region genes (see for example, WO 90/10077 and WO 90/04036). Alternatively, the antibody of interest may be engineered by recombinant DNA techniques to substitute the $C_{H1}$, $C_{H2}$, $C_{H3}$, hinge domains, and/or the framework residues with the corresponding human sequence (see WO 92/02190). Humanized antibodies against apoE are of particular interest for in vivo use in humans, and may be used as a therapy for Alzheimer's disease.

The antibodies utilized in the present invention may also be used to produce chimeric antibodies. The use of Ig cDNA for construction of chimeric Ig genes is known in the art (Liu et al. (1987) *Proc. Natl. Acad. Sci.* 84:3439; Liu et al. (1987) *J. Immunol.* 139:3521). mRNA is isolated from a hybridoma or other cell producing the antibody. and used to produce cDNA. The cDNA of interest may be amplified by the polymerase chain reaction using specific primers (U.S. Pat. Nos. 4,683, 195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The chimeric, humanized antibody is then expressed by conventional methods.

Expression vectors for use in modification of the antibodies of the invention are well known in the art and include plasmids, retroviruses, yeast artificial chromosomes (YACs), EBV derived episomes, and the like. For example, where the apoE is to be modified to provide a human antibody heavy and/or light chain constant region, a convenient vector is one that encodes a functionally complete human $C_H$ or $C_L$ Ig sequence, with appropriate restriction sites engineered so that any $V_H$ or $V_L$ sequence can be easily inserted and expressed. In such vectors, splicing usually occurs between the splice donor site in the inserted J region and the splice acceptor site preceding the human C region, and also at the splice regions that occur within the human $C_H$ exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Biol.* 3:280), Rous sarcoma virus LTR (Gorman et al. (1982) *Proc. Natl. Acad. Sci.* 79:6777), and Moloney murine leukemia virus LTR (Grosschedl et al. (1985) *Cell* 41:885); native Ig promoters, etc.

Biological Samples

Biological samples to be analyzed using the methods of the invention are obtained from any mammal, e.g., a human or a non-human animal model of AD. In some embodiments, analysis is performed on a post mortem sample. In many embodiments, the biological sample is obtained from a living subject.

In some embodiments, the subject from whom the sample is obtained is apparently healthy, where the analysis is performed as a part of routine screening. In other embodiments, the subject is one who is susceptible to AD, (e.g., as determined by family history; exposure to certain environmental factors; etc.). In other embodiments, the subject has symptoms of AD (e.g., memory loss, etc.). In other embodiments, the subject has been provisionally diagnosed as having AD (e.g. as determined by cognitive testing).

The biological sample may be derived from any tissue, organ or group of cells of the subject. In some embodiments a bodily fluid, e.g., blood, urine, cerebrospinal fluid, saliva, lymph, etc. is obtained from a subject. A bodily fluid, e.g., blood, is obtained by known techniques (e.g. venipuncture). Also included by the term "biological samples" are products of the tissues, organ or group of cells from a subject. In some embodiments, e.g., blood is sub-fractionated into blood products before analysis, where blood products include plasma, blood lysates, serum, etc. In many embodiments, the biological sample includes any organ, tissue, cell, or fluid sample that is not brain or brain derived.

In some embodiments, the biological sample is processed, e.g., to remove certain components that may interfere with an assay method of the invention, using methods that are standard in the art. In some embodiments, the biological sample is processed to enrich for proteins, e.g., by salt precipitation, and the like.

In the assay methods of the invention, in some embodiments, a comparison between a level of carboxyl-truncated apoE in a biological sample and a level of carboxyl-truncated apoE in a control sample is made. Suitable control samples are from individuals known to be healthy, e.g., individuals known not to have AD. Control samples can be from individuals genetically related to the subject being tested, but can also be from genetically unrelated individuals. A suitable control sample also includes a sample from an individual taken at a time point earlier than the time point at which the test sample is taken, e.g., a biological sample taken from the individual prior to exhibiting possible symptoms of AD.

Utility

The methods of the instant invention for determining the level of carboxyl-truncated apoE in a biological sample are useful for a variety of diagnostic analyses. The instant methods are useful for diagnosing AD in an individual; for determining a patient's response to treatment for AD; for determining the severity of AD in an individual; and for monitoring the progression of AD in an individual.

Methods of diagnosing AD may be performed on biological samples from living subjects, or post mortem. Methods for determining a patient's response to treatment for AD; for determining the severity of AD in an individual; and for monitoring the progression of AD in an individual are generally performed on living subjects. A particularly advantageous feature of the invention is that diagnosis can be made using aqueous biological tissues, such as blood and serum, which are readily available for sampling from the living.

Alzheimer's Disease Diagnosis

Where a level of carboxyl-truncated apoE in a biological sample is above the level of carboxyl-truncated apoE associated with a control sample, a diagnosis of Alzheimer's disease is indicated.

An increase in the level of carboxyl-truncated apoE in a biological sample from an individual (a "test sample"), compared to the level of carboxyl-truncated apoE in a control sample from a healthy individual, of from about 25% to about 20-fold, e.g., an increase of from about 25% to about 50%, from about 50% to about 100% (or 2-fold), from about 2-fold to about 2.5-fold, from about 2.5-fold to about 3.0-fold, from about 3.0 fold to about 3.5-fold, from about 3.5-fold to about 4.0-fold, from about 4.0-fold to about 5.0-fold, from about 5.0-fold to about 6.0-fold, from about 6.0-fold to about 7.0-fold, from about 7.0-fold to about 8.0-fold, from about 8.0-fold to about 10-fold, or from about 10-fold to about 20-fold, indicates that the individual has AD.

In some embodiments, the level of carboxyl-truncated apoE in a test sample in comparison to the level of carboxyl-truncated apoE in a control sample is expressed as a ratio. In these embodiments, a ratio of the level of carboxyl-truncated apoE in a test sample to the level of carboxyl-truncated apoE in a control sample of from about 1.5 to about 15, e.g., from about 1.5 to about 2.0, from about 2.0 to about 2.5 or more, from about 2.5 to about 3.0, from about 3.0 to about 3.5, from about 3.5 to about 4.0, from about 4.0 to about 5.0, or from about 5.0 to about 10 or more is an indication that the subject has AD. A determination of AD can be made using a standard curve of statistically significant values.

In other embodiments, the ratio of carboxyl-truncated apoE to total apoE in a test sample is compared to the ratio of carboxyl-truncated apoE to total apoE in a control sample. In these embodiments, an increase in the ratio of carboxyl-truncated apoE to total apoE in a test sample, compared to that of a control sample of from about 25% to about 20-fold, e.g., an increase of from about 25% to about 50%, from about 50% to about 100% (or 2-fold), from about 2-fold to about 2.5-fold, from about 2.5-fold to about 3.0-fold, from about 3.0 fold to about 3.5-fold, from about 3.5-fold to about 4.0-fold, from about 4.0-fold to about 5.0-fold, from about 5.0-fold to about 6.0-fold, from about 6.0-fold to about 7.0-fold, from about 7.0--fold to about 8.0-fold, from about 8.0-fold to about 10-fold, or from about 10-fold to about 20-fold, indicates that the individual has AD.

In other embodiments, the ratio of carboxyl-truncated apoE to full-length apoE in a test sample is compared to the ratio of carboxyl-truncated apoE to full-length apoE in a control sample. In these embodiments, an increase in the ratio of carboxyl-truncated apoE to full-length apoE in a test sample, compared to that of a control sample of from about 25% to about 20-fold, e.g., an increase of from about 25% to about 50%, from about 50% to about 100% (or 2-fold), from about 2-fold to about 2.5-fold, from about 2.5-fold to about 3.0-fold, from about 3.0 fold to about 3.5-fold, from about 3.5-fold to about 4.0-fold, from about 4.0-fold to about 5.0-fold, from about 5.0-fold to about 6.0-fold, from about 6.0-fold to about 7.0-fold, from about 7.0-fold to about 8.0-fold, from about 8.0-fold to about 10-fold, or from about 10-fold to about 20-fold, indicates that the individual has AD.

Severity of Disease

The instant methods are useful to assess the severity of AD. The severity of AD can be assessed by comparing the detected levels of carboxyl-truncated apoE with levels of carboxyl-truncated apoE in samples, and associating the level with the severity of AD.

In this embodiment, a relatively very high level of carboxyl-truncated apoE is usually associated with severe (i.e. highly progressed) AD, a relatively high level of carboxyl-truncated apoE is usually associated with moderate AD, and an above normal but not high relative carboxyl-truncated apoE level is usually associated with mild AD. The severity of the disease may allow the selection of more efficacious therapies, for example a mild case of AD may be more susceptible to certain drugs than a severe case.

Alzheimer's Disease Monitoring

The instant methods are useful for monitoring the progression of AD. Determining carboxyl-truncated apoE levels at different times is used to monitor the progression of AD. A biological sample is taken from the individual and tested at a frequency of once per week, twice weekly, once per month, bimonthly, once every three months, once every four months, once every 6 months, or once a year, depending on various factors.

In these embodiments, the level of carboxyl-truncated apoE in a test sample is compared to the level of carboxyl-truncated apoE in a previous sample(s). An increase in the level of carboxyl-truncated apoE in a test sample, compared to one or more previous test samples, indicates that the disease is increasing in severity.

The rate of increase in the level of carboxyl-truncated apoE is an indication of the rate of progression of the disease.

Response to Treatment

The instant methods are also useful to determine a patient's response to a treatment for AD. Measurements of carboxyl-truncated apoE levels are used to determine whether a patient is responding to treatment. In some embodiments, carboxyl-truncated apoE levels are measured before and after a treatment, e.g. brain surgery or a drug treatment, to determine if the treatment is efficacious. In other embodiments, carboxyl-truncated apoE levels are determined during the course of the treatment, to determine whether the treatment slows the progression of the disease, and to what extent the treatment slows the progression of the disease. For example, a reduction of at least about 10%, at least about 20%, at least about 25%, at least about 30%, or at least about 40% or more, in the rate of increase in the level and/or ratio of carboxyl-truncated apoE in response to a given treatment indicates that the treatment is efficacious in treating AD.

Kits

The present invention also includes kits for carrying out the methods of the invention. A subject kit comprises an antibody specific for a carboxyl-truncated form of apoE. In some embodiments, the antibody comprises a detectable label. In other embodiments, a secondary labeling component, such as a detectably labeled secondary antibody, is included. In some embodiments, a subject kit further comprises an antibody specific for the C-terminal portion of apoE. In some embodiments, a subject kit further comprises a means, such as a device or a system, for separating the carboxyl-truncated apoE from the sample.

A subject kit can further include, if desired, one or more of various conventional components, such as, for example, containers with one or more buffers, detection reagents or antibodies. Printed instructions, either as inserts or as labels, indicating quantities of the components to be used and guidelines for their use, can also be included in the kit. In the present disclosure it should be understood that the specified materials and conditions are important in practicing the invention but that unspecified materials and conditions are not excluded so long as they do not prevent the benefits of the invention from being realized. Exemplary embodiments of the diagnostic methods of the invention are described above in detail.

In a subject kit, the apoE detection reaction may be performed using an aqueous or solid substrate, where the kit may comprise reagents for use with several separation and detection platforms such as test strips. In many embodiments of the test strip kit, the test strip has bound thereto a first immobilized capture antibody that specifically binds the C-terminal portion of apoE and captures the full length apoE; a second immobilized capture antibody that binds and captures carboxyl-truncated apoE. In some embodiments, the kit further comprises a detection antibody, which is either directly or indirectly detectable, , and which binds and allows the quantification of the relative carboxyl-terminal truncated apoE levels. Kits may also include components for conducting western blots (e.g., pre-made gels, membranes, transfer systems, etc.); components for carrying out ELISAs (e.g., 96-well plates); components for carrying out immunoprecipitation (e.g. protein A); columns, especially spin columns, for affinity or size separation of carboxyl-truncated apoE from full length apoE (e.g. gel filtration columns, antibody columns, size exclusion columns, membrane cut-off spin columns etc.).

Subject kits may also contain a control full-length apoE/carboxyl-truncated apoE dilution series, where the dilution series represents a range of appropriate standards with which a user of the kit can compare their results and estimate-the level of carboxyl-truncated apoE in their sample. Such a dilution series may be a mixture of carboxyl-truncated apoE and full-length apoE, at, for example weight ratios of 0.02 (i.e. 2 µg of carboxyl-truncated apoE for every 100 µg of full-length apoE), 0.04, 0.06, 0.08, 0.10, 0.12, 0.14, 0.16, 0.18 and 2.0. Fluorescence, color, or autoradiological film development results may also be compared to a standard curves of fluorescence, color or film density provided by the kit.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric. Standard abbreviations may be used, e.g., bp, base pair(s); kb, kilobase(s); pl, picoliter(s); s, second(s); min, minute(s); hr, hour(s); and the like.

Example 1

Characterization of Carboxyl-Terminal Truncated apoE Expression Levels

Methods and Materials

Protein-A agarose was from Boehringer Mannheim. Recombinant human apoE3, apoE4, apoE3(Δ277-299), or apoE4(Δ277-299) were expressed in *E. coli* and purified using established techniques. Polyclonal anti-human apoE antibody was from Calbiochem. Anti-apoE-carboxyl-terminal antibody (amino acids 277-299) was obtained by passing the polyclonal anti-apoE antibody for three times through a Sepharose CL-4B column that was coupled with a mixture of apoE3(Δ277-299) and apoE4(Α277-299). The unbound fraction was used as anti-apoE-carboxyl-terminal antibody. Complete removal of antibodies against apoE-amino terminal portion (amino acids 1-271) was confirmed by western blotting on full-length apoE and apoE(Δ277-299).

Plasma samples (4 µl) from 20 Alzheimer's disease patients (10 with an apoE3/3 genotype and 10 with an apoE4/3 genotype) and 20 age matched non-demented controls (10 with apoE3/3 genotype and 10 with an apoE4/3 genotype) were analyzed by anti-human apoE western blotting.

Results

Western blotting using anti-full-length apoE polyclonal antibody revealed both full-length apoE and apoE products with a molecular mass of 14-20 KDa. Anti-C-terminal apoE (amino acids 277-299) only recognized the full-length apoE but not the fragments of apoE with a molecular mass of 14-20 kDa, showing that the 14-20 kDa fragments are C-terminal truncated forms of apoE. The pattern of the C-terminal truncated apoEs in the circulation is very similar to that seen in human brains of AD patients and transgenic mice expressing human apoE4 specifically in CNS neurons. Quantitative analysis by scanning the western blotting autoradiographs demonstrated that the ratios of the C-terminal truncated apoE to the full length apoE were significantly higher in AD patients with either apoE3/3 or apoE4/3 genotypes than in age-matched non-demented controls with the corresponding apoE3/3 or apoE4/3 genotype (FIG. 1). Finally, there was a trend to higher truncated apoE:full length apoE ratios in AD patients with an apoE4/3 genotype than in AD patients with an apoE3/3 genotype.

Similar results were obtained from a repeat study in which 80 more samples were included (20 samples for each group). Again, the ratios of the C-terminal truncated apoE to the full length apoE were significantly higher in AD patients with either apoE3/3 or apoE4/3 genotypes than in age-matched non-demented controls with the corresponding apoE genotype. For these 80 new samples, there were also higher ratios of the truncated apoE to full length apoE in AD patients with an apoE4/3 genotype than in AD patients with an apoE3/3 genotype.

It is evident from the above results and discussion that the subject invention provides an important new means for diagnosis, prognosis and monitoring of the progression of Alzheimer's disease. Specifically, the subject invention provides a system for detecting the levels of carboxyl-truncated apoE in a biological sample, where the sample is a bodily fluid of a living subject. As such, the subject methods and systems find use in a variety of different applications, including research, medical, therapeutic and other applications. Accordingly, the present invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for diagnosing Alzheimer's Disease (AD) in a living individual, the method comprising detecting a level of carboxyl-terminal truncated apolipoprotein E (apoE) in an aqueous biological sample from the individual, wherein the carboxyl-terminal truncated apoE comprises amino acids 244-260 of apoE, and wherein the carboxyl-terminal truncated apoE is a form such that a level of the carboxyl-terminal truncated apoE that is significantly higher than the level present in a normal control indicates that the individual has AD.

2. The method of claim 1, wherein the biological sample is blood.

3. The method of claim 1, wherein the biological sample is serum.

4. The method of claim 1, wherein the carboxyl-terminal truncated apoE has a molecular weight of about 14-20 kDa.

5. The method of claim 1, wherein apoE is apoE4.

6. The method of claim 1, wherein apoE is apoE3.

7. The method of claim 1, wherein apoE is a mixture of apoE3 and apoE4.

8. The method of claim 1, further comprising detecting a level of full length apolipoprotein E (apoE) in the biological sample from the individual; wherein a ratio of the level of carboxyl-terminal truncated apoE compared to the level of full length apoE in the biological sample that is greater than a ratio associated with a control biological sample from an individual not having Alzheimer's Disease is indicative of a diagnosis of Alzheimer's Disease.

9. The method of claim 8, wherein the carboxyl-terminal truncated apoE has a molecular weight of about 14-20 kDa.

10. The method of claim 8, wherein a ratio of the level of carboxyl-terminal truncated apoE compared to the level of full length apoE in the biological sample that is at least 25% greater than a ratio associated with a control biological sample from an individual not having Alzheimer's Disease is indicative of a diagnosis of Alzheimer's Disease.

11. The method of claim 8, wherein a ratio of the level of carboxyl-terminal truncated apoE compared to the level of full length apoE in the biological sample that is at least 50% greater than a ratio associated with a control biological sample from an individual not having Alzheimer's Disease is indicative of a diagnosis of Alzheimer's Disease.

12. The method of claim 8, wherein a ratio of the level of carboxyl-terminal truncated apoE compared to the level of full length apoE in the biological sample that is at least 2-fold greater than a ratio associated with a control biological sample from an individual not having Alzheimer's Disease is indicative of a diagnosis of Alzheimer's Disease.

13. The method of claim 1, wherein the biological sample is plasma.

14. The method of claim 1, wherein the biological sample is cerebrospinal fluid.

15. A kit for diagnosing Alzheimer's Disease, the kit comprising; a) an antibody that binds to carboxyl-terminal truncated apolipoprotein E (apoE) wherein the carboxyl-terminal truncated apoE comprises amino acids 244-260 of apoE; and b) instructions for using the antibody for diagnosing Alzheimer's Disease.

16. The kit of claim 15, further wherein the antibody is attached to a solid support.

17. The kit of claim 16, wherein the solid support is a test strip.

18. The kit of claim 15, further comprising an antibody that specifically binds to a carboxyl-terminal portion of full-length apoE.

19. The kit of claim 18, wherein the antibody that specifically binds to a carboxyl-terminal portion of apoE binds specifically to an epitope within amino acids 270-299 of apoE.

20. The kit of claim 15, wherein the instructions for the diagnosis of Alzheimer's Disease direct the use of the kit to detect carboxyl-terminal truncated apoE in serum.

* * * * *